United States Patent
Safai et al.

(10) Patent No.: US 8,220,991 B2
(45) Date of Patent: Jul. 17, 2012

(54) ELECTROMAGNETICALLY HEATING A CONDUCTIVE MEDIUM IN A COMPOSITE AIRCRAFT COMPONENT

(75) Inventors: Morteza Safai, Seattle, WA (US); Kimberly D. Meredith, Bellevue, WA (US); Gary E. Georgeson, Federal Way, WA (US); Gregory John Clark, Seattle, WA (US); Jeffrey Lynn Duce, Milton, WA (US)

(73) Assignee: The Boeing Company, Chicago, IL (US)

( * ) Notice: Subject to any disclaimer, the term of this patent is extended or adjusted under 35 U.S.C. 154(b) by 969 days.

(21) Appl. No.: 12/195,396

(22) Filed: Aug. 20, 2008

(65) Prior Publication Data

US 2008/0304539 A1 Dec. 11, 2008

Related U.S. Application Data

(63) Continuation-in-part of application No. 11/383,018, filed on May 12, 2006, now Pat. No. 7,568,832.

(51) Int. Cl.
*G01K 7/00* (2006.01)

(52) U.S. Cl. .......... 374/163; 374/5; 324/240; 156/272.2

(58) Field of Classification Search .................. 374/163, 374/5, 10–11, 57, 121; 324/525, 219, 228, 324/238–240, 512; 156/64, 94, 98, 307.1, 156/307.7, 272.2, 272.4; 382/141
See application file for complete search history.

(56) References Cited

U.S. PATENT DOCUMENTS

| | | | |
|---|---|---|---|
| 4,312,212 A * | 1/1982 | Clendenin | 374/53 |
| 4,327,743 A | 5/1982 | Katz | |
| 4,760,493 A * | 7/1988 | Pearson | 361/218 |
| 5,035,230 A | 7/1991 | Steidl et al. | |
| 5,293,119 A * | 3/1994 | Podney | 324/242 |
| 5,400,040 A * | 3/1995 | Lane et al. | 343/700 MS |
| 5,408,881 A * | 4/1995 | Piche et al. | 73/582 |
| 5,417,494 A | 5/1995 | Kempa et al. | |
| 5,513,537 A * | 5/1996 | Brooks et al. | 73/865.8 |
| 5,582,485 A * | 12/1996 | Lesniak | 374/5 |
| 5,709,469 A * | 1/1998 | White et al. | 374/5 |
| 5,902,935 A | 5/1999 | Georgeson et al. | |
| 6,004,817 A | 12/1999 | Chamberlain et al. | |
| 6,052,086 A * | 4/2000 | Kudoh | 343/700 MS |
| 6,220,099 B1 | 4/2001 | Marti et al. | |
| 6,234,025 B1 | 5/2001 | Gieske et al. | |
| 6,335,703 B1 * | 1/2002 | Chang et al. | 343/700 MS |
| 6,394,646 B1 * | 5/2002 | Ringermacher et al. | 374/7 |
| 6,636,037 B1 * | 10/2003 | Ou-Yang | 324/240 |
| 6,748,791 B1 | 6/2004 | Georgeson et al. | |
| 6,759,659 B2 * | 7/2004 | Thomas et al. | 250/341.6 |
| 6,843,130 B2 | 1/2005 | Georgeson | |
| 6,848,312 B2 | 2/2005 | Georgeson | |
| 6,945,111 B2 | 9/2005 | Georgeson | |
| 7,083,327 B1 * | 8/2006 | Shepard | 374/46 |
| 7,171,033 B2 * | 1/2007 | Engelbart et al. | 382/141 |
| 7,287,902 B2 * | 10/2007 | Safai et al. | 374/5 |
| 7,513,964 B2 * | 4/2009 | Ritter et al. | 156/64 |
| 7,568,832 B2 * | 8/2009 | Safai et al. | 374/10 |
| 7,889,907 B2 * | 2/2011 | Engelbart et al. | 382/141 |

(Continued)

*Primary Examiner* — Lisa Caputo
*Assistant Examiner* — Tania Courson

(57) ABSTRACT

Nondestructive examination is performed on a composite aircraft component including a composite body and a conductive medium. The conductive medium is substantially more conductive than the composite body. The nondestructive examination includes applying an electromagnetic field that penetrates the composite body and heats the conductive medium, and creating a thermal image of the conductive medium to reveal conductivity information about the conductive medium.

20 Claims, 6 Drawing Sheets

U.S. PATENT DOCUMENTS

2003/0041854 A1 3/2003 Sabin et al.
2004/0065981 A1 4/2004 Grimmer et al.
2006/0274812 A1 12/2006 Safai et al.

* cited by examiner

FIG. 2b
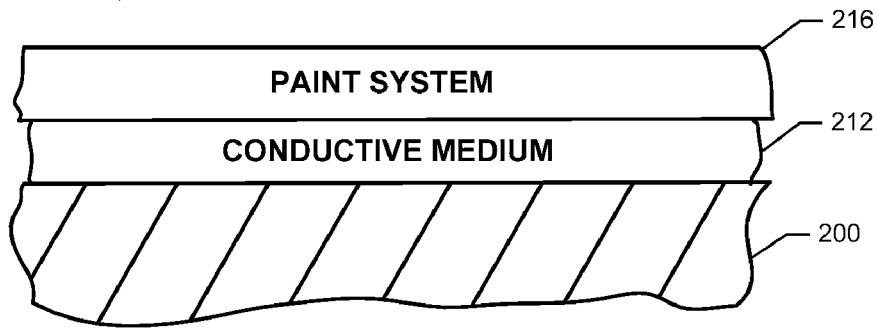
FIG. 2c
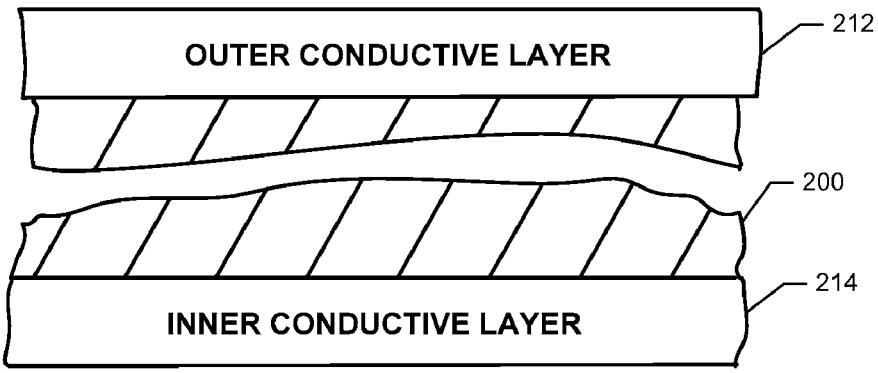
FIG. 3
```
APPLY AN ELECTROMAGNETIC FIELD THAT
PENETRATES COMPOSITE MATERIAL AND       — 310
HEATS A CONDUCTIVE MEDIUM
                    |
                    ▼
CREATE A THERMAL IMAGE OF THE
CONDUCTIVE MEDIUM TO REVEAL             — 320
CONDUCTIVITY INFORMATION
```

FIG. 7
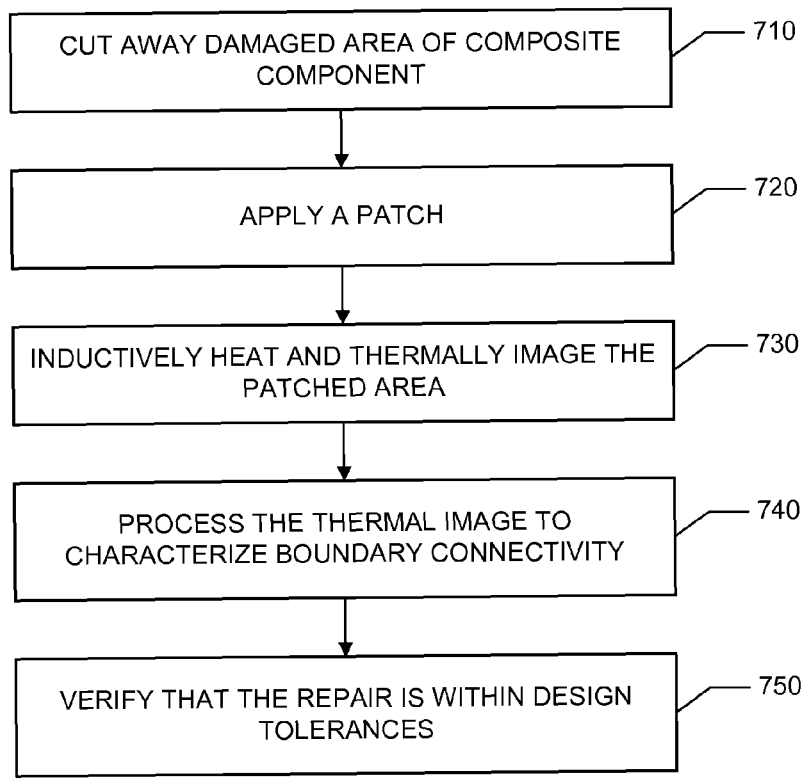
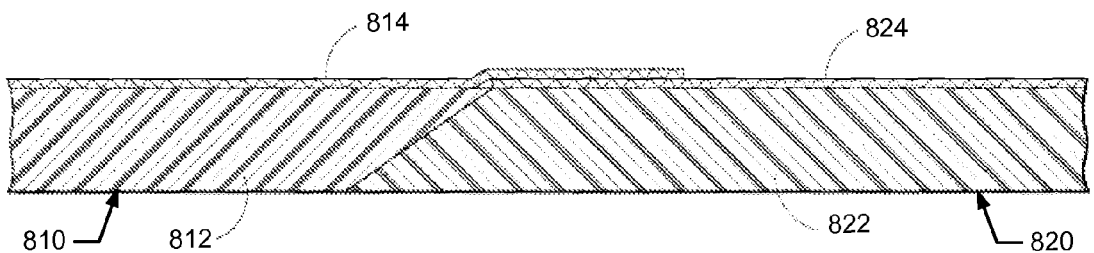
FIG. 8

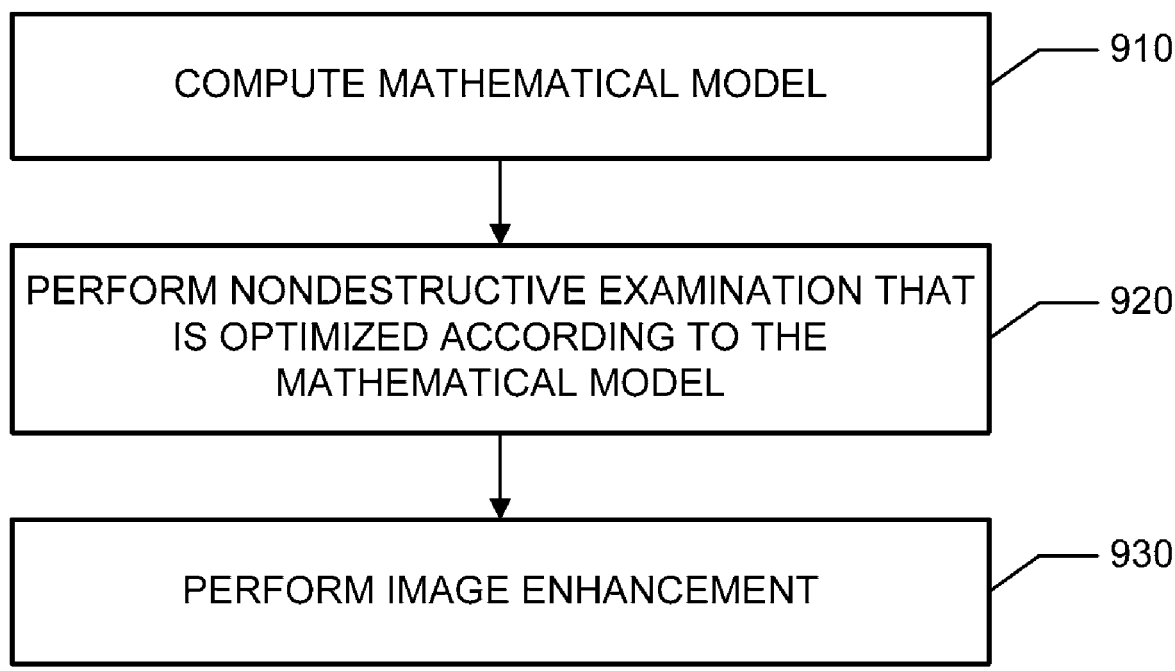

ELECTROMAGNETICALLY HEATING A CONDUCTIVE MEDIUM IN A COMPOSITE AIRCRAFT COMPONENT

BACKGROUND

Lightweight composite materials hold great promise for the aircraft industry. Fiber composites provide a significant improvement in specific strength and stiffness over conventional metal alloys. Better specific strength and stiffness translates into weight savings, which translates into fuel savings and lower operating costs. Additionally, composites do not corrode like aluminum, and they are more resistant to fatigue.

General aviation aircraft and large commercial jets are vulnerable to lightning strike. Unlike aircraft structures made of metal, composite structures do not readily conduct away the extreme electrical currents and electromagnetic forces generated by lightning strikes.

To ensure safety of flight, aircraft with composite structures may be equipped with lightning strike protection (LSP) features. For example, conductive media can be provided on a surface of or embedded in a composite structure to divert current away from metal fasteners and other flight-critical components.

On occasion, a lightning strike will damage a composite structure containing an LSP feature. The damaged area may be repaired by cutting it away and replacing it with a composite patch.

The patch should have a good conductive path to the surrounding material. Conductivity may be assessed by ohmic testing. For instance, a 2 or 4 point probe may be used to take direct electrical conductivity measurements. However, such measurement tends to be inconsistent due to variability of probe placement, differences between the conductivity of the fibers and resin, and the directional and layered structure of different plies of the fibers. The probe tips might make contact with different ratios of fiber to resin, they might not align along fibers, and they might touch fibers on different plies. Slight relative motion between a test point and a handheld probe can also lead to inconsistent measurement.

Moreover, making the measurements can be very tedious, as the conductivity is measured along the probe axis, between probe tips where the current passes. The areas examined are relatively small.

Nondestructive examination for rapidly and reliably assessing the conductive path would be highly desirable because of the potentially large areas that may need to be measured, and the need to get aircraft back into service as quickly as possible.

SUMMARY

According to an embodiment herein, nondestructive examination is performed on a composite aircraft component including a composite body and a conductive medium. The conductive medium is substantially more conductive than the composite body. A method of performing the non-destructive examination includes applying an electromagnetic field that penetrates the composite material and heats the conductive medium, and creating a thermal image of the conductive medium to reveal conductivity information about the conductive medium.

According to another embodiment herein, a method of performing nondestructive examination on a composite aircraft component comprises applying an electromagnetic field to an area of interest on the component. The component includes a fiber-based composite body and a layer containing metal. The electromagnetic field induces eddy currents in the layer. The method further comprises creating a thermal image of the area to reveal conductivity information about the metal in the layer.

According to another embodiment herein, a method of performing non-destruction examination of traces that are embedded in a composite aircraft component includes applying an electromagnetic field to an area over the traces. The electromagnetic field induces eddy currents in the traces. The method further includes creating a thermal image of the area, and examining the thermal image to determine conductivity information about the traces.

BRIEF DESCRIPTION OF THE DRAWINGS

FIGS. 2a-2c are illustrations of composite aircraft components that carry conductive media.

FIG. 3 is an illustration of a method of a performing nondestructive examination of a composite aircraft component.

FIG. 7 is an illustration of a method of repairing a composite aircraft component.

FIG. 8 is an illustration of a composite component that has been patched.

FIG. 9 is an illustration of a method of performing nondestructive examination of a circuit embedded in a composite component.

DETAILED DESCRIPTION

Figure 1:
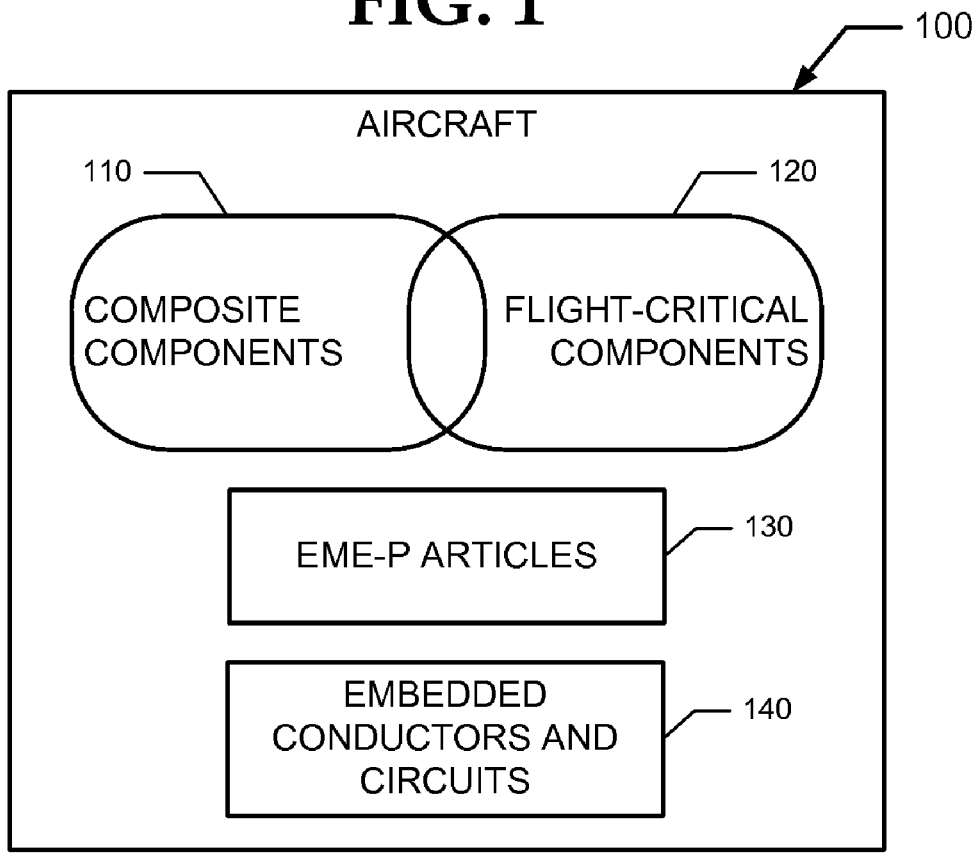
FIG. 1 is an illustration of an aircraft including composite aircraft components.

Reference is made to FIG. 1, which illustrates an aircraft 100 including a plurality of composite components 110. Composite components 110 such as skins, ribs, spars and stringers are joined together to form major components such as wings, fuselage and empennage. The composite components 110 may include a composite material such as fiberglass or Carbon Fiber Reinforced Plastic (CFRP).

The aircraft 100 also includes flight-critical components 120. Flight-critical components in general are components that affect the flight-worthiness of the aircraft 100. Certain composite components 110 might also be flight-critical (as represented by the intersection of 110 and 120).

Some of the composite components 110 are provided with one or more articles 130 that provide protection against lightning strike and other forms of electromagnetic effect (EME). These EME protection ("EME-P") articles 130, when assembled to their composite components 110, divert and distribute high EME currents away from flight-critical components 120. The diverted current is distributed over a larger area so that dangerous concentrations do not develop in any one place. An EME-P article 130 may include a metallic layer that is patterned (a mesh, for example) or solid.

Some of the composite components 110 may include embedded metallic conductors (e.g., traces) and embedded circuits 140. For instance, metallic traces can provide electrical connectivity for sensors and components. Examples of embedded sensors and components include, but are not limited to, embedded passive readout devices (EPRDs), embedded active readout devices (EARDs), Rogowski coils for current measurement, thermopiles, thermistors, fuses, radio frequency identification devices (RFIDs), conductive nanostructures, MEMS and strain gauges. These sensors and components can provide a variety of applications in communications, mitigation of electromagnetic interference (EMI), real time monitoring of the health and condition of flight-critical components and other aircraft systems, real time monitoring of temperature and mechanical excursions, de-icing circuitry, and tuned antenna networks.

Figure 2A:
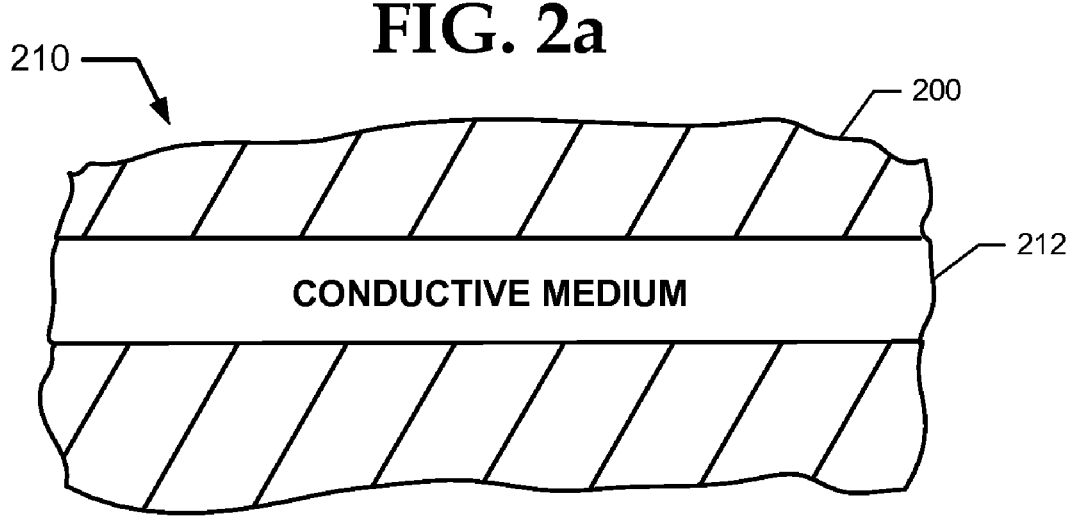

Reference is made to FIGS. 2a-2c, which illustrate different arrangements of conductive media with respect to composite aircraft components 210, 220 and 230. Each component includes a composite body 200. All components carry at least one conductive medium. The composite body 200 may be somewhat electrically conductive. However, each conductive medium is substantially more conductive than the composite body 200. For example, each conductive medium may have the conductivity of a metal such as copper.

The component 210 of FIG. 2a includes a conductive medium 212 embedded within the composite body 200. The conductive medium 212 could be an EME-P article or a conductive trace.

The component 220 of FIG. 2b has a conductive medium 212 between a composite body 200 and a paint system 216. The conductive medium 212 could be an EME-P article.

The component 230 of FIG. 2c carries two conductive media: an outer layer 212 that is on or near the surface of the composite body 200, and an inner layer 214 that is embedded within the composite body 200. For example, the outer layer 212 may be an EME-P article, and the inner layer 214 may include metallic traces.

Reference is now made to FIG. 3, which illustrates a method of performing nondestructive examination of a composite aircraft component. The method includes applying an electromagnetic field to the composite aircraft component (block 310). A coil may be used to apply the electromagnetic field. Excitation frequencies for the coil may be in the range of 100 kHz to 400 kHz. This range has been found to create an electromagnetic field that penetrates the composite material.

Eddy currents are induced in the conductive medium by a changing magnetic field. For example, a changing magnetic field can result from relative motion of the coil and the conductive medium; or due to variations of the electromagnetic field with time. The stronger the applied electromagnetic field, or the greater the electrical conductivity of the conductive medium, or the greater the relative velocity of motion, the greater the eddy currents developed.

Conductive materials such as aluminium and copper have a very high electrical conductivity and will produce far greater eddy currents than composite material, which has a relatively low electrical conductivity and much less coupling, and is much thicker. Eddy currents also occur in composites at much lower frequencies.

The coil's excitation current can be pulse width modulated to allow for controlled heating. The induced currents heat the conductive medium.

The frequency or frequencies actually used to excite the coil will depend on the thickness to penetrate. Lower frequencies offer deeper penetration.

The excitation frequency might also depend on depth and conductivity of conductive medium, structures surrounding the conductive medium (e.g., the composite body), etc.

Inductive heating with an electromagnetic field offers advantages over heating with microwaves. Microwaves are limited in penetration of conductive materials and will not work with graphite/carbon fiber composites of any real thickness. In general, microwaves will only heat a conductive medium if that conductive medium is on the surface of a composite material.

The method further includes creating a thermal image of the conductive medium to reveal conductivity information about the conductive medium (block 320). In some embodiments, the thermal image may be created with a thermal imaging camera. In other embodiments, the thermal image may be created with by a thermographic film on a surface of the composite component. The thermographic film is temperature-sensitive and generates an optically viewable representation of the heated area. The thermographic film is described in greater detail in the assignee's U.S. Pat. No. 7,287,902.

Layers at different depths may be heated by varying the frequency of the electromagnetic field. Appropriate frequencies can be selected to heat conductive media within, on or behind the composite. For example, a frequency can be selected to penetrate an LSP layer and inspect circuit traces below the LSP layer.

An appropriate frequency can be selected to heat the composite. Heating the composite can have certain advantages. Wrinkles, cracks, and other defects or damage may be found by inducing eddy currents into composites. Also, bonding between composite and a non-conductive media could be assessed, since heat does not transfer well across disbonds, and the resulting hot spots can be identified by thermal imaging.

Figure 4:
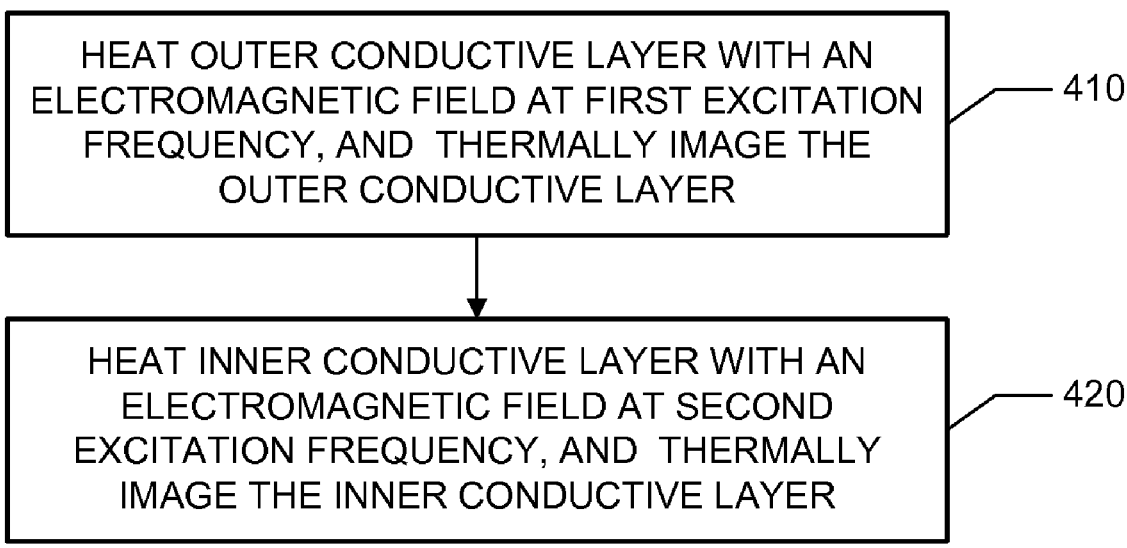
FIG. 4 is an illustration of a method of varying the depth of examination.

Reference is now made to FIG. 4. Consider the component 230 illustrated in FIG. 2c. The outer conductive layer 212 is heated with an electromagnetic field at a first excitation frequency, and the outer conductive layer 212 is thermally imaged (block 410). Next, the inner conductive layer 214 is heated with an electromagnetic field at a second excitation frequency, and the inner conductive layer 214 is thermally imaged (block 420).

Figure 5:
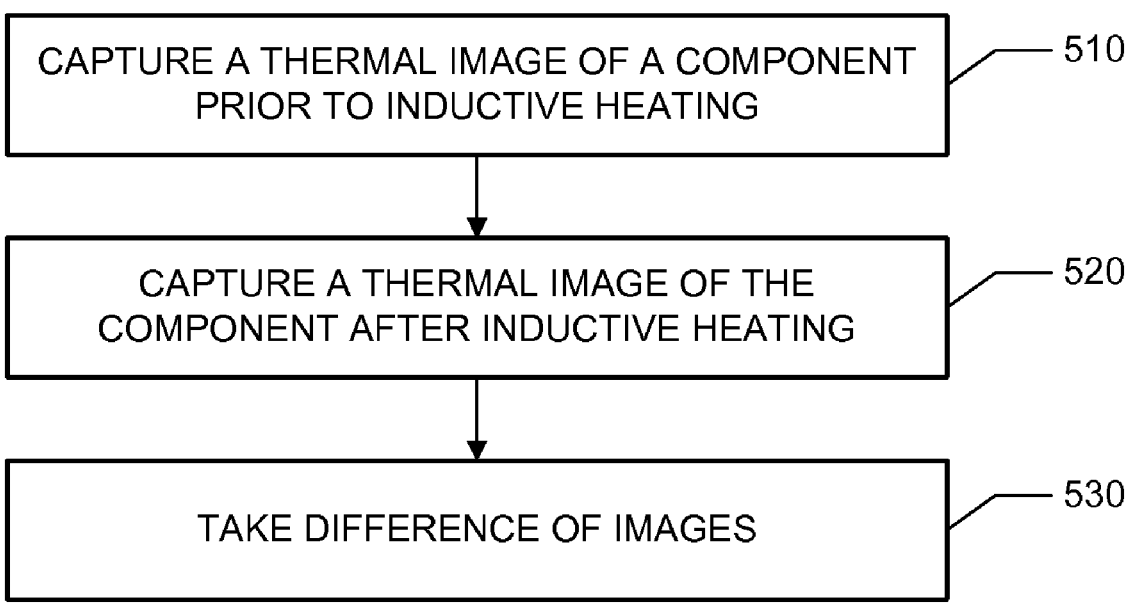
FIG. 5 is an illustration of a method of computing a difference image.

Reference is now made to FIG. 5. In some embodiments, thermally imaged features may be highlighted by taking a difference of two images. A difference of two images may be taken as follows. Prior to inductive heating, a thermal image of a component is captured (block 510). Then inductive heating is performed, and the component is thermally imaged once again (block 520). A difference image is obtained by taking the difference of these two captured images (block 530).

A difference of two images allows selected images on the heating or cooling curve to be subtracted out. These selected images might highlight key features or surface features that influence an infrared image. Thus, these key features and surface features can be subtracted out.

Additional differences can be collected and stored, for averaging purposes. This process can continue for several seconds. Once the current excitation has been turned off, the subtracted images can be integrated in order to generate a composite image. This technique, known as synchronized thermography, allows for detection of small thermal gradients and reduction of noise in IR imaging.

Additional image processing may be performed on the difference image. For example, Fourier filtering, edge enhancement and Laplacian filtering may be applied to the difference image.

Detection capability may also be enhanced. For instance, detection capability may be enhanced by coating the surface with a high emissivity paint in order to obtain better IR signals and reduce reflections from the surface.

Figure 6:
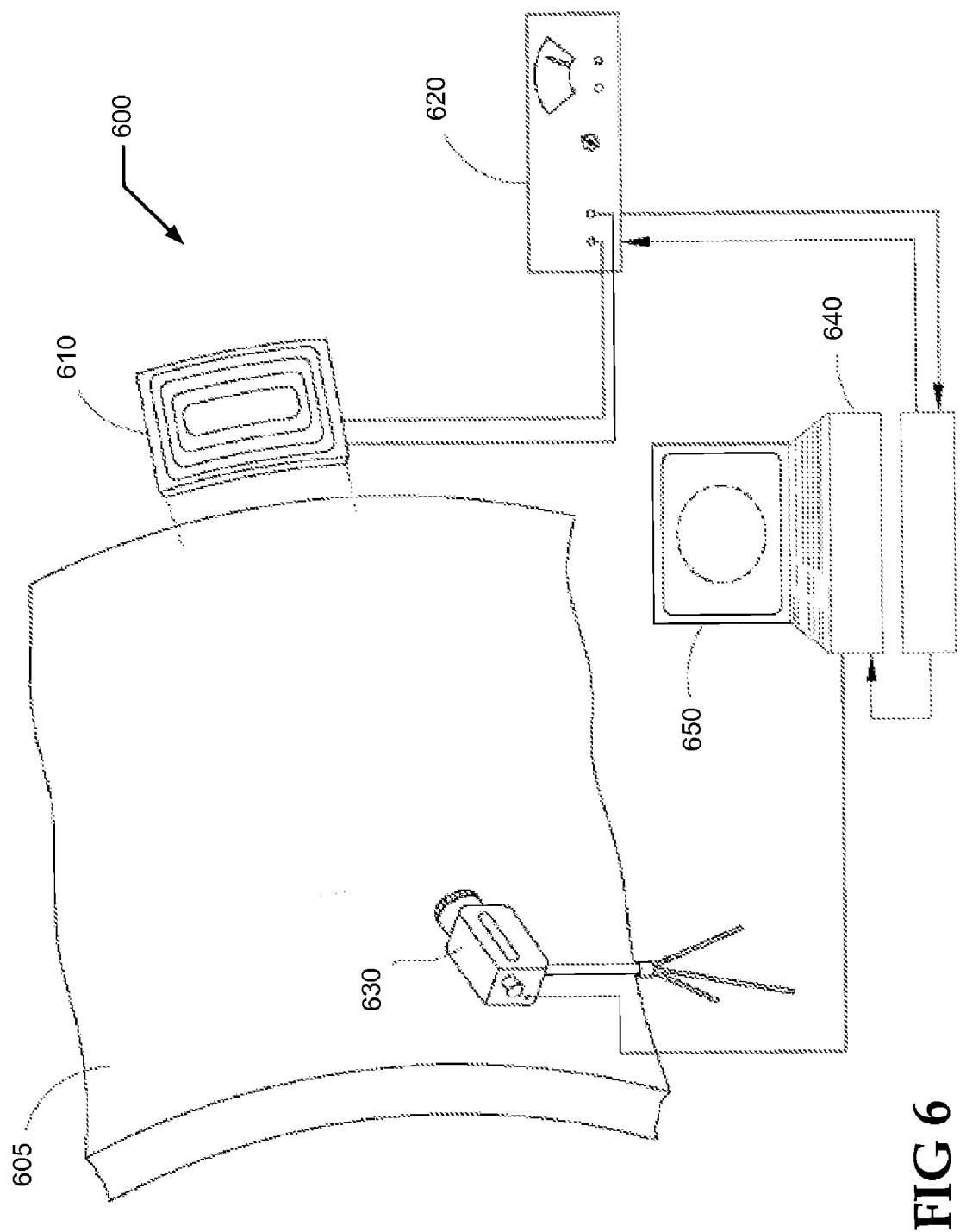
FIG. 6 is an illustration of a system for performing nondestructive examination of a composite aircraft component.

Reference is now made to FIG. 6, which illustrates a system 600 for performing nondestructive examination of a composite aircraft component. The system 600 includes a high power induction coil 610 that is provided with a controllable power supply 620. Placing the powered coil 610 in proximity to a component 605 induces eddy currents in the component's conductive medium. A thermal imaging camera 630 is directed at a surface of the component 605 and has a field of view that encompasses all or part of the heated area. The camera 630 captures one or more images of the component 605.

A computer data acquisition and control system 640 processes the captured images and provides control of the power supply 620 for various thermal imaging techniques. Camera data (raw or processed or both) may be displayed on a monitor 650 and stored in memory for additional processing.

In some embodiments, the thermal imaging camera 630 may include a focal plane array (FPA) detector, which may or may not be cryogenically cooled. In some embodiments, a camera image frame can be synchronized with current pulses so an image can be obtained before the current is applied and then captured after the current has been applied.

In some embodiments, the electromagnetic field may be applied omni-directionally. An advantage of an omni-directional field is that all conductive features will be heated, regardless of their orientation.

In some embodiments, the electromagnetic field may be a directional. For example, an elongated coil may be used to apply a directional electromagnetic field. A directional magnetic field is advantageous for selectively heating features that are oriented in a particular direction. For example, directional heating may be used to selectively heat fibers, wires, and other elongated conductive media.

The coil 610 could be shaped to conform to the surface of the component being inspected. In some embodiments, a non-flat surface of a single coil could be shaped by applying an external force. In some embodiments, a non-flat surface could be formed by multiple coils having different lengths. Such coils could be advantageous for structures having complex shapes.

In some embodiments, the coil 610 may be waved over the area to be inspected. The desired motion of the coil 610 and its distance from the component surface are dependent on the power level of the coil, RF frequency of the coil, the coil shape and size, etc.

In some embodiments, an automated system may be used to create coil motion. For instance, this motion may be accomplished using a three axis positioning device with motion along the surface of the component 605.

The thermal images can reveal discontinuities in a conductive medium. However, the thermal image can reveal additional information as discussed below.

Reference is now made to FIG. 7, which illustrates a method of repairing a damaged area of a composite aircraft component, where the component includes an EME-P article. At block 710, the damaged area of the composite component is cut away, along with the EME-P article in the damaged area. One or more edges of the EME-P article may be sanded or etched to reveal the copper or other conductive medium.

At block 720, a patch is applied to the cut-away area. The patch includes a portion made of metal and a portion made of composite material. The composite portion may be a pre-preg or a cured composite material.

Additional reference is made to FIG. 8. The composite portion 812 of the patch 810 abuts against the composite body 822 of the component 820. The metallic portion 814 of the patch 810 overlaps edges of the EME-P article 824. The overlap is exaggerated for clarity. The overlap produces a region around the patch where the electrical contact needs to be assured for continuity of the EME-P article.

The composite portion 812 of the patch 810 may be bonded to or co-cured with the composite body 822 of the component 820. The metallic portion 814 of the patch 810 may be bonded to the EME-P article with a conductive adhesive. In the alternative, the patch 810 may be applied to the EME-P article as a decal with integral pressure sensitive adhesive, or secondarily bonded using heat and pressure with a vacuum bag and hot bonder.

At block 730, the patched area is inductively heated and thermally imaged. The thermal images are believed to reveal current flow changes (e.g., current build-up at thinning connections, zero current at breaks, etc.)

At block 740, the thermal image is processed to characterize boundary connectivity. A well-bonded patch 810 will have a uniform thermal image across the boundary of the patch area. Connectivity and current density in the connections between metallic portion 814 of the patch 810 and the EME-P article are revealed by thermal "peaks", thermal "plateaus", and thermal valleys in the thermal image. A well-bonded patch will have a uniform thermal image, while thermal "peaks" demonstrate high current density and thermal "plateaus" demonstrate low current density, with thermal valleys demonstrating complete breaks/no conduction.

At block 750, it is verified that the repair is within design tolerances. The thermal image and analysis thereof provides an assurance of good contact between the patch and EME-P medium. If the contact is not good, the repair can be repeated.

Reference is now made to FIG. 9, which illustrates a method of examining traces that are embedded in a composite component. The traces may be part of circuits that also include elements such as inductors, resistors, switches and connectors.

At block 910, prior to performing nondestructive examination, a mathematical model is computed. The model may indicate the maximum amount of current that may be induced without damaging the circuit. The model may provide information about heat dissipated by the substrate on which the circuit is formed. The model may provide information about shielding of magnetic field as it affects the induced eddy currents.

At block 920, nondestructive examination is performed. The mathematical model may be used to optimize the nondestructive examination. The model may provide information about what the infrared images should look like, the best shape of the coil, frequency and thermal heating and differential required for infrared detection the amount of wattage, etc.

The nondestructive examination may be performed with an image processor, thermal camera, and coil as described herein. Once the image processor and camera are actively acquiring image data, the coil is turned on and heat is applied. Then, image data is recorded real time, where it can be analyzed later.

When current is induced into a closed circuit, the entire circuit will heat up enough to be imaged with the infrared camera. However if the circuit is open, only the areas where the current is directly being applied will heat up, due to the heating of the induced current paths. Thus, relatively light areas (indicating higher heat) will correspond to good traces, while relatively dark areas (indicating lower heat) will correspond to open circuits. In other embodiments, the dark and light contrast can be reversed.

A method herein not only identifies whether a circuit has discontinuities, but it can also identify the locations of any discontinuities. The circuit can be examined very rapidly. The thermal images identify not only embedded circuitry, but can differentiate between closed and open circuits. It doesn't just image the physical dimensions of the circuits, but highlights regions of reduced conductivity and open circuits.

The thermal images offer even more information. The thermal images can also reveal intensity gradients. Thus, the images can also provide information about resistivity profiles.

Variations in traces can be identified. These variations might be used to assess the manufacturing process, since the variations might be caused by non-uniformity and contaminants. For instance, traces are formed by vapor deposition, and the vapor deposition process is assessed by examining the images for thickness, width and uniformity of the traces.

At block 930, image processing software can be used for common image enhancement techniques, such as subtraction, filtering, normalization and thermal derivatives (e.g., first derivatives, second derivatives). The image processing software could enhance features such as edges and shapes sensitive to minor current differences. If thermal images are stored in a raw digital format, they could be compensated for gain and offset without concern about exceeding the maximum temperature range. This would provide better sensitivity to features of interest, without worrying about automatic gain control for displaying the image. In addition, the use of raw data allows noise level to be reset and the area of interest to be selected on data at any point and time.

The invention claimed is:

1. A method of performing nondestructive examination of a composite aircraft component including a composite body and conductive medium, the conductive medium being substantially more conductive than the composite body, the method comprising:
applying an electromagnetic field that penetrates the composite body and heats the conductive medium; and
creating a thermal image of the conductive medium to reveal conductivity information about the conductive medium.

2. The method of claim 1, wherein the electromagnetic field induces eddy currents in the conductive medium.

3. The method of claim 2, wherein the electromagnetic field is applied by a coil, and wherein excitation frequency of the coil is in the range of 100 kHz to 400 kHz.

4. The method of claim 1, wherein a directional electromagnetic field is applied to heat the conductive medium.

5. The method of claim 1, wherein the aircraft component includes at least two layers of conductive media at different depths, and wherein frequency of the electromagnetic field is varied to heat a selected layer.

6. A method of repairing a composite aircraft structure that carries an electromagnetic effect protection article, the method comprising:
applying a patch to a damaged area of the electromagnetic effect protection article, the patch including a conductive layer that is electrically connected to the electromagnetic effect protection article;
applying the electromagnetic field to an area that encompasses the patch and creating a thermal image of the area, the field applied and the image created according to claim 1; and
examining the thermally imaged area to identify any electrical discontinuities between the patch and the electromagnetic effect protection article.

7. A method of performing non-destructive examination of a circuit that is embedded in a composite aircraft component, the method comprising:
applying the electromagnetic field to an area that encompasses the circuit and creating a thermal image of the area, the field applied and the image created according to claim 1; and
examining the thermally imaged area to determine conductivity information about the embedded circuit.

8. The method of claim 7, wherein examining the thermally imaged area includes examining thermal gradients to identify discontinuities in circuit traces.

9. The method of claim 7, wherein examining the thermally imaged area includes examining trace thickness to evaluate a process used to manufacture circuit traces in the circuit.

10. The method of claim 7, wherein examining the thermally imaged area includes determining a resistivity profile of traces in the circuit.

11. The method of claim 1, wherein creating the thermal image includes taking a difference of images to highlight features of interest.

12. The method of claim 1, further comprising creating eddy currents in the composite body to heat the body; wherein the thermal image also identifies defects in the composite body.

13. The method of claim 1, further comprising using a mathematical model of the component to optimize the heating and imaging.

14. A method comprising performing nondestructive examination on a composite aircraft component including a fiber-based composite body and a layer containing metal, including:
applying an electromagnetic field to an area of interest on the component, the electromagnetic field inducing eddy currents in the layer; and
creating a thermal image of the area to reveal conductivity information about the metal in the layer.

15. The method of claim 14, wherein the layer is an upper layer that provides EME protection for the component; wherein the component also includes a lower layer containing metal traces, and wherein eddy currents are selectively induced in each layer and a thermal image of each layer is created.

16. The method of claim 14, wherein the layer is part of a patch, the patch repairing a damaged area of the component, the layer adhered to an electromagnetic effect protection article of the component; and wherein the thermal image of the area indicates whether the layer makes a good electrical connection with the electromagnetic effect protection article.

17. The method of claim 14, wherein the layer includes metal traces of an embedded circuit; and wherein the thermal image of the area indicates conductivity information about the traces.

18. A method of performing non-destruction examination of metal traces that are embedded in a composite aircraft component, the method comprising:
applying an electromagnetic field to an area over the traces, the electromagnetic field inducing eddy currents in the traces;
creating a thermal image of the area; and
examining the thermal image to determine conductivity information about the traces.

19. The method of claim 18, wherein examining the thermally imaged area includes examining thermal gradients to identify discontinuities in the traces.

20. The method of claim 18, wherein examining the thermally imaged area includes examining trace thickness to evaluate a process used to manufacture the traces.

* * * * *